United States Patent [19]

Opsal et al.

[11] Patent Number: 5,042,952
[45] Date of Patent: * Aug. 27, 1991

[54] METHOD AND APPARATUS FOR EVALUATING SURFACE AND SUBSURFACE AND SUBSURFACE FEATURES IN A SEMICONDUCTOR

[75] Inventors: Jon Opsal, Livermore; Allan Rosencwaig, Danville; Walter L. Smith, Livermore, all of Calif.

[73] Assignee: Therma-Wave, Inc., Fremont, Calif.

[*] Notice: The portion of the term of this patent subsequent to Apr. 1, 2003 has been disclaimed.

[21] Appl. No.: 550,333

[22] Filed: Jul. 9, 1990

Related U.S. Application Data

[63] Continuation of Ser. No. 351,540, May 15, 1989, Pat. No. 4,952,063, which is a continuation of Ser. No. 76,876, Jul. 23, 1987, Pat. No. 4,854,710, which is a continuation of Ser. No. 707,485, Mar. 1, 1985, abandoned, which is a continuation-in-part of Ser. No. 612,076, May 21, 1984, Pat. No. 4,636,088.

[51] Int. Cl.$^5$ ................. G01N 21/41; G01N 25/00
[52] U.S. Cl. ................................ 356/432; 356/445
[58] Field of Search ................. 356/432, 432 T, 445

[56] References Cited

U.S. PATENT DOCUMENTS

| | | | |
|---|---|---|---|
| 4,211,488 | 7/1980 | Kleinknecht | 356/432 |
| 4,243,327 | 1/1981 | Frosch et al. | 356/432 |
| 4,579,463 | 4/1986 | Rosencwaig et al. | 356/445 |

OTHER PUBLICATIONS

Cerdeira et al, "Photoreflectance and Electroreflectance in Silicon", *Solid State Communications*, vol. 7, pp. 879-882, 1969.

Shay, J. L., "Photoreflectance Line Shape at the Fundamental Edge in Ultrapure Galts", *Physical Review B*, vol. 2, No. 4 (Aug. 15 1970), pp. 803-807.

*Primary Examiner*—Richard A. Rosenberger
*Attorney, Agent, or Firm*—Limbach, Limbach & Sutton

[57] ABSTRACT

A method and apparatus are disclosed for evaluating surface and subsurface features in a semiconductor sample. In operation, a periodic energy source is applied to the surface of the semiconductor sample to generate a periodic electron-hole plasma. This plasma interacts with features in the sample as it diffuses. The plasma affects the index of refraction of the sample and the changing plasma density is monitored using a radiation probe. In the preferred embodiment, the radiation probe measures the plasma induced periodic changes of reflectivity of the surface of the sample to yield information about the sample, such as ion dopant concentrations, residue deposits and defects.

5 Claims, 2 Drawing Sheets

METHOD AND APPARATUS FOR EVALUATING SURFACE AND SUBSURFACE AND SUBSURFACE FEATURES IN A SEMICONDUCTOR

This is a continuation of application Ser. No. 07/351,540, filed May 15, 1988 now U.S. Pat. No. 4,952,063, which is a continuation of application Ser. No. 07/076,876, filed July 23, 1987, now U.S. Pat. No. 4,854,710, issued Aug. 8, 1989 which is a continuation application Ser. No. 707,485, filed Mar. 1, 1985, now abandoned, which is a continuation-in-part of application Ser. No. 612,076, filed May 21, 1984, now U.S. Pat. No. 4,636,088, issued Jan. 13, 1987.

TECHNICAL FIELD

The subject invention relates to a new and improved method and apparatus for evaluating surface and subsurface features in a semiconductor. Information is derived by analyzing the interaction between sample features and an electron-hole plasma induced in the sample variations in plasma density, which is in part, a function of variations in the sample, are measured based on the effect of the plasma on the refractive index at the surface of the sample. A radiation probe is reflected off the surface of the sample and changes induced in the radiation probe by the plasma-induced changes in the refractive index are monitored to obtain information about surface and subsurface characteristics of the sample.

BACKGROUND OF THE INVENTION

There has been considerable effort expended in developing tools for the nondestructive analysis of materials. This interest is particularly strong in the integrated circuit industry. In the prior art, techniques were developed where high powered optical microscopes are used to analyze surface characteristics of a sample Subsurface features have been analyzed through the use of acoustic waves that are generated in the sample and interact with the elastic features beneath the surface of the sample. More recently, a new branch of investigations has developed wherein thermal waves are used to derive information about thermal features in a sample.

In a thermal wave system, a localized periodic heating is induced at the surface of the sample Energy from the heat source is absorbed by the sample at or near its surface and a periodic surface heating occurs at the modulation frequency of the heat source. This periodic surface heating is the source of thermal waves that propagate from the heated region. The thermal waves interact with thermal boundaries and barriers in a manner that is mathematically equivalent to scattering and reflection of conventional propagating waves. Thus, any features on or beneath the surface of the sample that have thermal characteristics different from their surroundings will reflect and scatter thermal waves and thus become visible to these thermal waves. Thermal waves can be induced in a wide variety of sample materials and can be used to detect these thermal features. Thermal waves, however, are critically damped and travel only about one thermal wavelength thus the penetration range is quite limited.

The subject invention is directed to a new and improved nondestructive analytical tool which in some respects is quite analogous to systems which perform thermal wave analyses In the subject invention, the density variations of a diffusing electron-hole plasma are monitored to yield information about features in a semiconductor.

As is well known, semiconductors have a band gap between the valence and conduction bands. Input energy is needed to raise an electron from the valence band to the conduction band which results in the creation of an electron-hole pair. Typically the input energy to the system will exceed the band gap energy and the electron will be excited from the valance band to an energy level above the conduction band. These electron carriers will, in a relatively short period of time ($\tau \simeq 10^{-13}$ seconds), give up a portion of their energy to the lattice through nonradiative transitions to the unoccupied states near the bottom of the conduction band. After a much longer time ($\tau = 10^{-3}$ to $10^{-8}$ seconds) these carriers will give up the remainder of their energy to the lattice by recombining with the holes of the valence band. Prior to this recombination, there exists a plasma of electrons and holes whose spatial density is governed by diffusion in a manner analogous to the flow of heat from a thermal source.

If an evaluation is made of this plasma diffusion, information can be derived about the composition and lattice structure of a semiconductor. In some situations, where the plasma is generated in a periodic fashion, "plasma waves" can be generated and information about subsurface features can be derived using an analysis similar to a thermal wave analysis.

Changes in plasma density will result in a change in the index of refraction at the surface of a sample. This dependance has been reported by D. H. Auston et. al., in "Picosecond Ellipsometry of Transient Electron-Hole Plasmas in Germanium" (*Physical Review Letters*, Vol 32, No. 20, May 20, 1974). This paper reports that changes in the index of refraction, due to the variations in plasma density, can be detected by reflecting a probe beam off the surface of the sample within the area which has been excited. (See also "Picosecond Time-Resolved Plasma and Temperature-Induced Changes of Reflectivity and Transmission in Silicon," J. M. Liu, et. al., *Applied Physics Letters* Vol. 41 No. 7 Oct. 1, 1982). These preliminary articles were merely attempting to analyze how the plasma moves through a sample. No effort was made to analyze the sample itself through the interaction of the plasma with the sample. Furthermore, the energy source was not modulated, that is, a periodic plasma was not generated, and thus would prevent an analysis similar to that described in the subject invention.

When the energy source is modulated and a periodic plasma is generated, the probe beam, which is reflected off the surface of the sample, will undergo periodic changes in both intensity and phase. Changes in intensity can be measured by a relatively simple photodetector technique. Changes in phase can be measured through monitoring by interferometry techniques or by monitoring the periodic angular displacements of a probe beam.

Very recently, some attempts have been made to analyze the plasma through its affects on acoustic waves generated in a silicon sample (See "Effect of Photocarriers on Acoustic Wave Propagation for Measuring Excess Carrier Density and Lifetimes in Silicon", Stearns, et. al., *Applied Physics Letters*, Vol. 45 No. 11, Dec. 1, 1984). In the experimental arrangement reported in this article, the energy source was modulated and a periodic plasma was generated. However, there was no attempt made to analyze the sample itself through interactions of the plasma with the sample. Furthermore, the analytical tool described in the latter article was a contact technique requiring an acoustic transducer.

In order to detect optical changes in the index of refraction it is necessary that the probe beam be located within the periodically excited area. The periodically excited area can be defined in terms of a radius with the center point being the center of the energy source as follows:

$$r = \sqrt{(r_o^2 + u^2)} \quad (1)$$

where $r_o$ is the radius of the energy source and u is the distance over which the plasma will diffuse in the sample. In the situation where the decay time $\tau$ (the time it takes for the electron-hole pairs to recombine) is relatively short compared to the modulation period $1/\omega$, where $\omega$ is the modulation frequency in radians/second, (i.e., $\omega\tau$ is less than 1) then the diffusion length (u) of the plasma is given by the following equation:

$$u = (D\tau)^{\frac{1}{2}} \quad (2)$$

where D is the diffusivity of the plasma.

A more interesting situation occurs when the decay time $\tau$ is long compared to the period of the modulation of the energy beam (i.e., $\omega\tau$ is greater than 1) In this case, "plasma waves" will be created and u is given by the following equation:

$$u = (2D/\omega)^{\frac{1}{2}} \quad (3)$$

These "plasma waves" are critically damped and can be analyzed in a manner directly analogous to thermal waves. More specifically, in this limiting case, the plasma diffusion length u depends on the modulation frequency $\omega$ and can therefore be varied by changing the modulation frequency. Information about the subsurface region as a function of depth beneath the sample surface is obtained by studying the periodic changes in the probe beam when the modulation frequency of the energy source is varied. This analysis is directly analogous to the studies described in detail in copending U.S. patent application Ser. No. 389,623 filed on June 18, 1982, and now U.S. Pat. No. 4,513,384, issued Apr. 23, 1985 assigned to the same assignee as the subject invention and incorporated herein by reference.

The analysis described in the latter patent application is intended to give information as to either layer thickness or compositional variables of a sample as a function of depth. These techniques can be applied with the method of the subject invention when the decay time $\tau$ is long compared to the period of modulation of the energy beam As described above, there are many important and significant similarities between thermal wave analysis and plasma density analysis, which is the subject of this application. There are also important differences. Most importantly, electron-hole plasma analysis is limited to semiconductor materials. However, when semiconductor analysis is desired, this technique provides some advantages over a thermal wave analysis. For example, plasma density analysis can be significantly more sensitive than a thermal wave analysis. Thermal wave studies only provide information as to thermal features plasma density analysis, which can be thought of as an analysis of the movement of highly interactive electrons, will provide information on a wide variety of changes in the structure and composition of a semiconductor sample. Furthermore, experiments have shown that the sensitivity of the plasma to variations in some sample characteristics can be anywhere from 10 to 100 times greater than that which would be expected from a thermal wave interaction alone.

Another distinguishing feature of this system is that unlike a thermal wave approach, a periodic heat source is not required. As pointed out above, in order to do a thermal wave analysis, it is necessary to induce a periodic localized heating on the sample surface to generate thermal waves. In the subject system, all that is required is a periodic energy source which will interact and excite electrons from the valance band to the conduction band. In practice, the means for exciting the plasma will be similar to those commonly used in generating thermal waves. However, it should be understood that the generation of heat is not required, and that it is only necessary to impart enough energy to the electrons to overcome the band gap in the sample. If this energy is carefully controlled, no localized heating will occur.

Another difference between the subject approach and thermal wave systems is that despite the fact that the energy beam is modulated, a "plasma wave" will not always be generated. As pointed out above, if the period of the modulated energy beam is greater than the recombinant or decay time ($\tau$), no plasma waves will be created In contrast, if the modulation frequency ($\omega$) is controlled such that the period between cycles is less than the decay time ($\tau$), plasma waves will be created.

For many measurement situations, a wavelike phenomenon, such as the plasma wave, is unnecessary for evaluation. For example, and as discussed in detail in the specification, applications which do not require depth profiling or the analysis of sample variations as a function of depth, do not require the generation of plasma waves. However, in applications where sample variations as a function of depth need to be studied, it is necessary to generate and study plasma waves.

Therefore, it is an object of the subject invention to provide a new and improved method and apparatus for evaluating surface and subsurface conditions in a semiconductor sample.

It is a further object of the subject invention to provide a new and improved method and apparatus for analyzing semiconductors wherein a sample is excited in a manner to create an electron-hole plasma.

It is another object of the subject invention to provide a method and apparatus wherein features in a semiconductor are anaylzed by generating an electronhole plasma in the sample and monitoring the diffusion of this plasma using a radiation probe.

It is a further object of the subject invention to provide a method and apparatus for evaluating surface and subsurface conditions in a semiconductor sample wherein changes in a reflected probe beam are monitored to study the density variations of the electron-hole plasma.

SUMMARY OF THE INVENTION

In accordance with these and many other objects, the subject invention provides for a new and improved apparatus and method for evaluating surface and subsurface conditions in a semiconductor sample More specifically, the subject invention is intended to permit nondestructive analysis of various properties of semiconductors. As discussed in greater detail below, the subject system is capable of detecting residues and defects, measuring ion dopant concentrations, and in the preferred embodiment, can also yield information relating to layer thicknesses and compositional variables as a function of depth.

In accordance with the subject invention, a means is provided for periodically exciting electrons in the sample to create electron-hole pairs or a plasma. The periodic energy can be supplied from a wide variety of sources including particle beams and chopped or modulated electro-magnetic radiation beams. In the preferred embodiment, an intensity-modulated laser beam is utilized.

As discussed above, the infusion of energy will result in the creation of an electron-hole plasma which propagates away from the energy source. The plasma will interact with surface and subsurface features of the sample such that the diffusion profile of the plasma will be altered The diffusion profile or changing density of the plasma is detected at the sample surface through the use of a radiation probe.

In accordance with the subject invention, the radiation probe is directed to the surface of the sample such that it falls within at least a portion of the area which is being periodically excited. The periodic changes in the plasma density will affect the index of refraction of the sample and thus cause periodic changes in the reflected radiation probe. These changes are then monitored and processed to evaluate the sample.

The radiation probe will undergo changes in both intensity and phase. In the preferred embodiment, the changes in intensity, caused by changes in reflectivity of the sample, are monitored using a photodetector. It is possible to detect changes in phase through interferometric techniques or by monitoring the periodic angular deflections of the probe beam.

Further analytical information can be obtained where the system is arranged to generate "plasma waves". More specifically, if the period between cycles of the energy beam is less than the decay time of the plasma, critically damped plasma waves will be created. These plasma waves may be treated analytically in a manner similar to critically damped thermal waves. A more complete mathematical presentation of plasma waves will be given below. While the use of thermal waves to evaluate surface and subsurface conditions is relatively new, a significant body of information already exists concerning methods of handling these analyses. Since the actual analyses are not a part of the subject invention, this disclosure will refer only to the portions that are necessary for understanding of the subject application. However, the above cited and following patents and patent applications should be referred to if a complete background of thermal wave analysis is desired. (See, Method For Detection of Thermal Waves With a Laser Probe, U.S. Ser. No. 401,511 filed July 26, 1982; and now U.S. Pat. No. 4,521,118 issued June 4, 1985. Thin Film Thickness Measurements with Thermal Waves, U.S. Ser. No. 481,275 filed Apr. 1, 1983; and now U.S. Pat. No. 4,522,510, issued June 11, 1985. Method and Apparatus For Evaluating Surface Conditions of a Sample, Ser. No. 612,076, filed May 21, 1984; and now U.S. Pat. No. 4,636,088 issued Jan. 13, 1987 and Method & Apparatus for Detecting Thermal Waves, U.S. Ser. No. 612,075, filed May 21, 1984 and now U.S. Pat. No. 4,579,463 issued Apr. 1, 1986. All the cited patents and applications are to the same assignee as the subject invention and their disclosures are incorporated herein by reference.

In a manner similar to that set forth in the above referenced disclosures, and in particular, U.S. Pat. No. 4,513,384, where plasma waves exists, additional information can be derived by varying the modulation frequency of the energy beam and observing changes in the observed plasma density. By varying the frequency of the energy beam, information can be obtained as to subsurface features, permitting analysis of layer thickness and composition variations as a function of depth. Further objects and advantages of the subject invention will become apparent from the following detailed description taken in conjunction with the drawings in which:

BEST MODE FOR CARRYING OUT THE SUBJECT INVENTION

Figure 1:
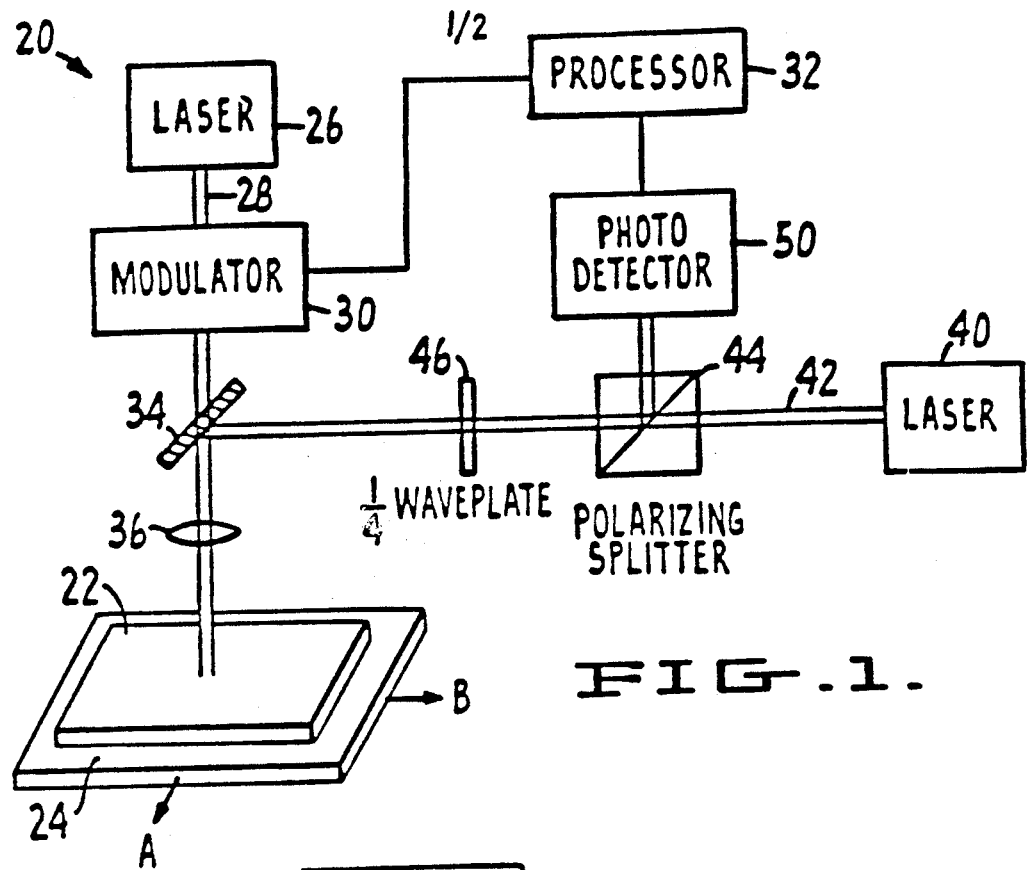
FIG. 1 is a schematic representation of an apparatus for performing the new and improved analysis on semiconductors of the subject invention.

Turning to FIG. 1, there is illustrated a schematic diagram of an apparatus 20 which performs the method of the subject invention. The particular apparatus illustrated is particularly adapted for detecting residues and defects and for microscopically evaluating ion dopant concentrations in a semiconductor by measuring changes in reflectivity of a probe beam.

Background information concerning the problems associated with the detection of residues and ion dopant concentrations is set forth in great detail in copending application, Ser. No. 612,076, cited above. Briefly, in many semiconductor manufacturing techniques, layers are successively deposited on a substrate and thereafter etched to define the desired circuitry. During many of these steps, it is possible that thin layers of residues will remain on the sample surface.

For example, an oxide layer is often deposited and then etched using a photoresist and masking technique during the fabrication of a semiconductor. In situations where neither the photoresist layer or oxide layer are fully removed, the integrated circuit will be prone to failures. To date, the industry has not come up with any good methods for detecting these residues. In most manufacturing situations, the integrated circuits are subjected to optical microscopic examination by human operators. As can be appreciated, this can be very time-consuming and inefficient. Furthermore, the thickness of the residues which can adversely affect the fabrication of the integrated circuits are so thin as to be nearly invisible, even when inspected through a microscope. Other techniques have been developed but they are not suitable for giving information with regard to the presence of residues within microscopically small regions.

Another technique in semiconductor manufacturing concerns the implantation of ion dopants. These dopants are implanted to impart different electrical conductivities to the substrate. In the implantation process, an ion beam is rastered over the surface of the sample. Some of the ions in the beam which bombard the sample are introduced into the lattice structure of the semiconductor. The concentration of the dopant ions in the sample is related to the length of time which the beam is focused on any point on the surface of the sample. The depth to which the ions penetrate is related to the voltage on the ion beam. However, even at a maximum voltage, the depth to which the ions penetrate is relatively small such that the ion concentrations of interest are substantially at the upper surface of the sample.

The ions which are incorporated into the surface of the sample are located at interstitial sites and physically disrupt the lattice structure of the material. In this state, the material will not exhibit the desired semiconductive properties. In order to overcome this problem, it is necessary to activate the dopant in a subsequent fabrication step. The dopant is activated through an annealing process. In this annealing process, the material is heated in a manner to permit the lattice to reform, enabling the ions to move from the interstitial sites to substitutional sites. In this process, the dopant ions are substituted for substrate atoms at various points in the lattice. This annealing step functions to remove defects in the lattice and free the electrons of the dopant ions for conduction of current.

Once the annealing step has been performed, the dopant levels which have been implanted usually can be measured by known electrical resistivity methods. However, these methods are unable to detect concentrations below $10^{13}$ ions per $cm^2$. The subject invention has been able to detect concentrations as low as $10^{10}$ ions per $cm^2$. In addition, the subject invention is also capable of detecting ion dopant concentrations prior to annealing which cannot be performed with an electrical measurement technique.

In a manner analogous to that used to detect implanted ions, many other types of microscopic impurities or defects can also be detected by the apparatus of the subject invention.

It will be noted that the above referenced patent No. 4,636,088 is directed to similar investigations based on the generation of thermal waves. It has now been found that when a semiconductor material is being tested, thermal waves do not have to be generated but, rather, investigations can be carried out by studying changing plasma density at the surface of the sample. When materials other than semiconductors are to be evaluated, such as, metals and dielectrics, periodic heating will still be necessary and analysis of the thermal wave patterns is required.

As set forth above, apparatus 20, is specifically designed for microscopic residue and defect detection and evaluation of dopant concentrations. Accordingly, apparatus 20 includes elements unnecessary to perform the more general aspects of applicant's new and improved method wherein electron-hole plasma interactions are studied. For example, information about a semiconductor on a more macroscopic scale will not require the use of a microscopic objective for focusing the energy and probe beams. Other elements which are illustrated in the apparatus of FIG. 1 which are not necessary for performing the basic steps of the subject invention will be discussed in the text.

In FIG. 1, there is illustrated a semiconductor test sample 22 which rests on a movable stage 24. Stage 24 is movable in two axes as shown by arrows A and B, enabling the sample to be rastered with respect to the energy and probe beams. By this arrangement, two-dimensional mapping of the surface and subsurface characteristics of the semiconductor can be readily achieved. Movable stages are well-known in the prior art and need not be described in detail herein.

As discussed above, sample 22 is a semiconductor By definition, a semiconductor will have a plurality of electrons in a valence band which can be excited across a band gap to a conduction band creating electron-hole pairs. In the literature, a plurality of these electron-hole pairs are called a plasma. In accordance with the subject invention, a means must be provided for exciting electrons in a manner to bridge the band gap and generate an electron-hole plasma. In the illustrated embodiment, the energy is supplied by a laser 26. The energy may be supplied through any source of electromagnetic radiation or even particle beams, such as an electron beam. The operation of the subject invention also requires that this energy source be periodic. Accordingly, the beam 28 which is emitted from laser 26 is chopped by a modulator 30. The chopping frequency of the modulator 30 is controlled by a processor 32 which also handles the controls of the detection portion of the device, discussed below.

As discussed above, the frequency of the modulator which chops the laser beam determines whether plasma waves will be generated. This threshold frequency is a function of the time it takes for the electron-hole pairs to recombine in the semiconductor. As can be appreciated, if the recombination time is shorter than the time of each laser pulse, any wave action will die out. However, if the plasma state exists for a time longer than the period of the modulation frequency, a wave-like phenomenon will be observed. A mathematical discussion of the characteristics of this wave-like phenomenon is disclosed in the attached Appendix. The generation of waves is necessary if it is desired to . perform some types of analyses involving depth profiling which are analogous to thermal wave detection systems. In the situation where depth information is not required, it is not a necessity that plasma waves be generated However, in practice, frequencies are often chosen which do in fact result in the production of plasma waves. In operation, it has been found that chopping frequencies on the order of one MHz to 100 MHz are most often utilized The frequency modulated laser beam 28 is directed to the surface of the semiconductor. As shown in FIG. 1, the beam 28 passes through a dichroic mirror 34 and a microscopic objective 36. The arrangement of the dichroic mirror and microscopic objective facilitate the focusing of the energy beam and the probe beam to microscopic spots on the surface of the sample. This arrangement is desirable where microscopic information is desired. In a preferred embodiment, laser 26 is an argon ion laser and the dichroic mirror is transparent to wavelengths emitted by such a laser. The dichroic mirror will reflect radiation emitted from a helium neon laser 40 which is used as the radiation probe.

As set forth in the subject invention, the energy level of laser 26 must be sufficient to excite electrons from the valence band to the conduction band of the semiconductor. This particular energy level is a function of the type of semiconductor which is being analyzed. The energy level of the laser beam can be chosen to match this band gap energy. If the laser beam has a higher energy than necessary, electrons will be excited above the band gap and then rapidly drop down to the lowest energy level of the conduction band. In the latter case, heat will immediately be generated and thermal waves will also be induced. It should be noted that when the electrons eventually drop from the conduction band down to the valence band, that is, when the electrons and holes recombine, additional heat may be released. Where additional heat is released in this latter step, its effect on the generation of thermal waves may have to be considered, particularly if the plasma has not diffused a significant distance.

In the situation where the laser energy is sufficient to generate electron-hole pairs, a plasma will be created which diffuses through the semiconductor. The plasma will affect the index of refraction of the semiconductor. More importantly, surface and subsurface features in the semiconductor will affect the movement or diffusion of the plasma and thereby alter its local density and resultant effects on the changes to the index of refraction.

In accordance with the subject invention, the changes in the index of refraction on the surface of the sample are monitored using a radiation probe. As illustrated in FIG. 1, the radiation probe is provided by a helium neon laser 40 which emits a beam 42 that is focused on the surface of the sample using dichroic mirror 34 and microscopic objective 36. As noted above, the dichroic mirror will reflect helium neon radiation. In order for the radiation probe to "see" the effects of the plasma, it must be directed within the periodically excited area This area is given by equation (1), cited above.

Where microscopic analysis is desired, further focusing through the use of a microscopic objective is desired. Typically, mirror 34 will also be moveable to facilitate positioning.

As is well-known, a beam of radiation has both intensity and phase characteristics. When the beam is reflected off a sample surface where the index of refraction is changing, the probe beam will experience both changes in intensity (because the reflectivity of the sample is changing) and changes in phase. The changes in reflectivity of the sample is given by the following equation:

$$\Delta R = (dR/dN)\Delta N \qquad (4)$$

where N is the plasma density and $dR/dN$ is the plasma density coefficient of reflectivity.

As can be seen from the above equation, if one can measure changes in reflectivity, one can monitor periodic changes in plasma density which are, in turn, a function of the surface and subsurface characteristics of the sample. The apparatus in FIG. 1 is designed to measure these changes in reflectivity. More particularly, probe beam 42 is passed through a polarizing splitter 44. The polarizing splitter is oriented in a manner such as to let the coherent light 42 emanating from laser 40 to pass freely therethrough. The splitter will, however, deflect all light whose phase has been rotated through 90° relative to beam 42. The reason for this arrangement will become apparent below.

Radiation probe beam 42 is then passed through a ¼-waveplate 46. Waveplate 46 functions to rotate the phase of the probe beam by 45°. As can be appreciated, on the return path of the beam, the waveplate will rotate the phase of the beam another 45° so that when it reaches splitter 44, the phase of the beam will have been rotated a total of 90° from the incoming orientation. By this arrangement, the splitter 44 will reflect the retroreflected light beam up to a photodetector 50, as discussed in more detail below.

After the probe beam passes through the ¼-waveplate 46, it is deflected downward by dichroic mirror 34. In the preferred embodiment of the subject invention, the energy beam 28 and the probe beam 42 are aligned in such a manner that they are directed in a coincident manner down through lens 36 and focused at essentially the same spot on the surface of the sample. By focusing the probe beam and the energy beam at the same spot, the maximum signal output can be achieved.

As the probe beam is reflected off the surface of the sample, it interacts with the sample at its surface. The refractive index of the sample undergoes periodic changes as the plasma density changes periodically. The probe beam essentially "sees" the changes of the index of refraction induced by the density changes of the plasma such that the intensity and phase of the probe beam will be altered.

The probe beam is then reflected back up to the dichroic mirror where it is, in turn, reflected back along the incoming path and through the ¼-waveplate 46. As discussed above, waveplate 46 rotates the phase of the probe beam by another 45° such that when the beam reaches splitter 44 it phase has been rotated 90° with respect to the original beam. Accordingly, the splitter will deflect the retroreflected probe beam upwardly towards photodetector 50.

Since intensity variations of a radiation beam are to be detected, a standard photodetector may be employed as a sensing mechanism. The intensity variations which are measured are then supplied as an output signal to processor 32 for deriving information relating to the surface and subsurface conditions of the sample. The processor will analyze changes which are in phase with the periodic changes of the energy beam 28. In practice, the apparatus of the subject invention has proved to be a highly sensitive indicator of the presence of residues and other defects, as well as levels of ion dopant concentrations in semiconductors.

This analysis is relatively straightforward in that the sample will typically be rastered with respect to the beams and the changing output signals which are in phase with the energy beam can be plotted to indicate variations in dopant or defect concentrations or the presence of residues. These output signals can be compared to predetermined reflectivity measurements made on a known reference sample. The latter information can be stored in the processor and compared to give relative information concerning the tested sample.

In this analysis, there is no necessity to ensure that plasma waves be generated. However, if one is interested in doing more sophisticated analysis of layer thickness or material composition as a function of depth, information can be derived by studying the interaction of plasma waves with the subsurface features. These plasma waves are highly damped such that they travel only one or two wavelengths before becoming too weak to detect. However, the plasma waves will interact with various microscopic features in the sample in a manner that is mathematically equivalent to scattering and reflection of conventional propagating waves. Any features on or beneath the surface of the sample that have electronic characteristics different from their surroundings will reflect and scatter the plasma waves and thus alter the diffusion of the plasma waves.

In order to ensure that plasma waves are generated, the frequency of the modulator must be set such that the modulation period is less than and preferably much less than the recombination time of the plasma. In a typical semiconductor sample of silicon, the recombination time is on the order of $10^{-5}$ seconds. Therefore, it is desirable to set the modulation frequency of the energy beam to be on the order of 1 MHz.

When plasma waves are generated, the diffusivity of the plasma is given by equation (3) above. As noted, in this situation, changes in beam modulation frequency will affect the plasma diffusion length. Thus, by varying the frequency of the modulator, one can derive additional information to calculate either layer thicknesses or compositional variables as a function of depth. The introductory mathematics for a plasma wave analysis is set forth below.

Calculations and measurements using these plasma waves are directly analogous to that of critically damped thermal waves. A number of approaches for deriving additional information using thermal waves is set forth in U.S. Pat. No. 4,513,384, cited above. In the latter application, sophisticated mathematical modeling is disclosed to provide in-depth analysis of surface and subsurface characteristics. Less sophisticated analysis is also possible in an online situation where measurements, taken on a known reference sample, while the frequency of the modulation of the energy beam is varied, are stored in the processor. These measurements can then be compared with a test sample to provide relative measurements and information regarding surface and subsurface features This approach can also be used in the method of the subject invention.

Figure 2:
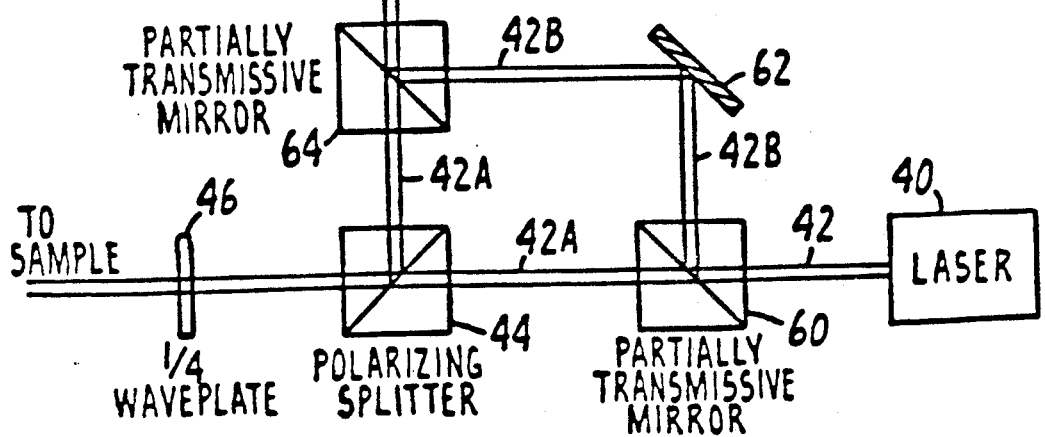
FIG. 2 is a schematic diagram, similar to FIG. 1, illustrating a structure wherein the changes in the probe beam can be monitored through an interferometric technique.

As discussed above, the change in the index of refraction of the sample 22 induced by the changing plasma density, will also alter the phase of the incoming probe beam. FIG. 2 shows an alternate apparatus, in schematic form, for measuring the phase changes in the probe beam 42. In FIG. 2, only the probe beam portions of the subject apparatus are illustrated with like numbers being used to designate like components.

As illustrated in FIG. 2, one method of detecting phase changes of an electromagnetic beam is through the use of an interferometry technique. Interferometers for measuring phase changes of lasers are well-known in the art. Furthermore, an interferometer has been used to measure thermal waves in an analogous manner. (See "Photo Displacement Imaging" Ameri et al., Photoacoustic Spectroscopy Meeting, *Technical Digest*, Paper THA6-1 Optical Society of America, 1981.)

Some theories exist as to the mechanism by which the phase of the probe beam will be shifted when the index of refraction of a material is changed. One theory relates to the changing of the path length of the beam prior to its being reflected. Where the index of refraction is changing periodically, the phase shift of the probe beam will vary in a sinusoidal manner. These phase shifts can be detected with an interferometer. It should be clear that an understanding of the the exact mechanism which causes the phase shift in the beam is not necessary to carry out the objects of the subject invention Rather, it is only necessary that this phase shift exists and can be measured. Furthermore, it is also important that this phase shift is a measure of the periodic changes in plasma density which is, in turn, dependent upon the surface and subsurface features of the sample.

As illustrated in FIG. 2, a laser is provided having a beam 42 which is passed through a partially transmissive mirror 60. A portion 42a of the beam will pass through the mirror and travel along a path through the polarizing splitter 44 and ¼-waveplate 46 in a manner identical to FIG. 1. Another portion of the beam 42b will also be reflected upwardly by the partially transmissive mirror 60 to an angled mirror 62. This portion 42b of the beam will be used as a reference for detecting the phase shift of the probe beam.

As in the first embodiment, the probe beam 42a is retroreflected off the surface of the sample back through the ¼-waveplate and directed upwardly by the polarizing splitter 44 to photodetector 50. Beam 42a will then pass directly through a partially transmissive mirror 64. Mirror 64 will also reflect the reference portion 42b of the probe beam upwardly into the photodetector 50.

At this point, the two portions of the radiation beam 42 have been recombined. As is well-known in the art, when two coherent beams of light are combined that are not in phase, interference patterns will develop. These interference patterns take the form of train of intensity variations which can be detected by the photodetector. In this application, since the phase shift of the probe beam 42a is constantly changing, the interference patterns will be constantly changing. These periodic intensity changes, brought about by the interference of the beams, are analyzed by the processor to field information about the plasma density variations in the sample. An analysis can then be made in a manner described above with regard to FIG. 1.

The phase changes are given by a formula analogous to the intensity change formula (4) as follows:

$$\Delta \Phi = (d\Phi/dN)\Delta N \tag{5}$$

where $\Phi$ is the phase and N is the plasma density.

Similar to the embodiment shown in FIG. 1, the probe beam 44a must be directed into the area that has been periodically excited by the energy beam. In addition, microscopic information can be obtained by focusing the beams through a microscopic objective 36.

Another measurement technique can also be used to monitor the phase changes in the probe. This alternative approach is analogous to the thermal wave detection technique disclosed in U.S. Pat. Nos. 4,521,118 and 4,522,510, cited above. In the latter techniques, the periodic angular deflections of the reflected probe beam are measured to give an indication of thermal wave activity. In the subject apparatus, the probe beam will also undergo periodic angular deflections in response to the plasma wave activity because of the radial variations in the plasma density.

Figure 3:
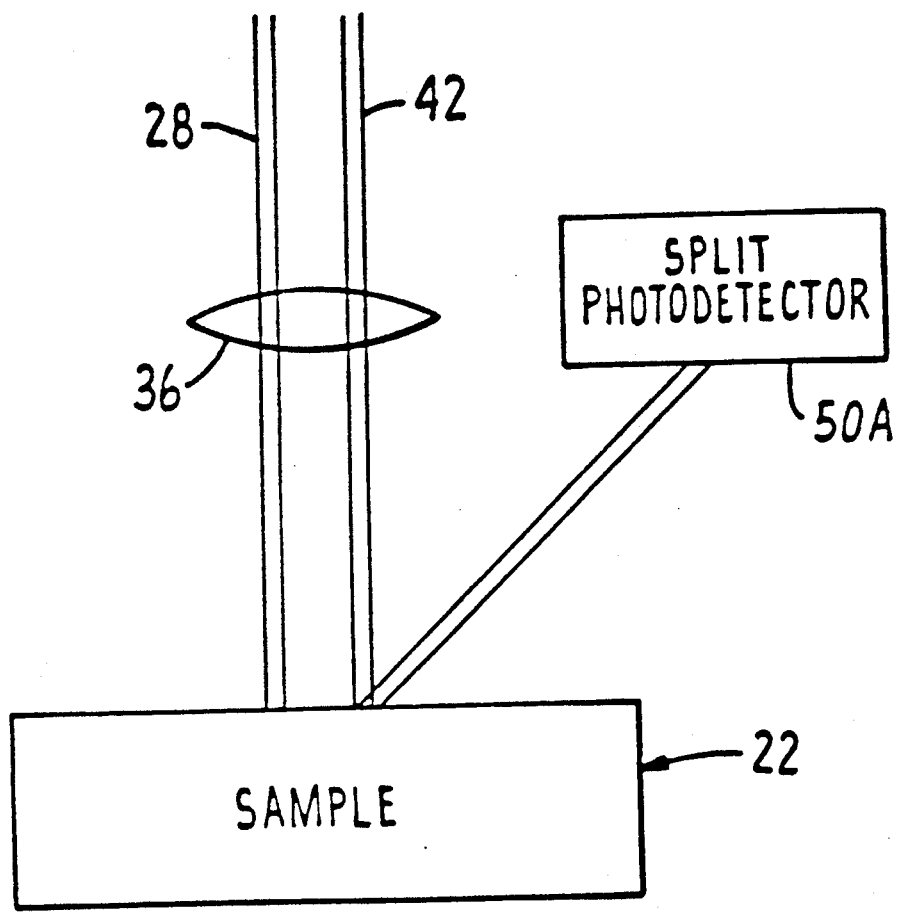
FIG. 3 is a partial schematic diagram illustrating an alternative embodiment wherein phase changes in the probe beam can be monitored by measuring the angular displacements of the probe beam.

A measurement system which can detect these periodic angular deflections can be provided by modifying the apparatus shown in FIG. 1. The elements which require modifications are shown in FIG. 3. Similar to FIG. 1, a periodic energy beam 28 and a probe beam 42 are directed to the surface of the sample 22. However, and as shown in FIG. 3, the changes in the probe beam are detected by a split or bi-cell photodetector 50a. Photodetector 50a has two quadrants, each of which gives a separate measure of the intensity of the beam. When the beam fluctuates across the surface of the detector, each side of the detector will experience changes in intensity which can be correlated by the processor to measure the extent of the beam deflections.

This form of detector is described in more detail in the applications cited above.

As set forth in the latter two patent applications, in order to maximize the signal in a deflection type technique, the probe beam 42 must be spaced from, but focused close to, the incoming energy beam 28. This arrangement is shown in FIG. 3 where microscope objective 36 is used to focus both beams. In this case, the mirrors are arranged such that the two beams are parallel but noncoaxial.

In summary, there has been provided a new and improved apparatus for evaluating surface and subsurface conditions in a semiconductor sample. In accordance with the subject invention, a periodic excitation source is provided for supplying energy to the sample surface sufficient to create an electronhole plasma. The diffusing plasma functions to change the index of refraction of the surface of the sample. The diffusion of the plasma is, in turn, a function of the local sample characteristics and thus the plasma induced changes in the index of refraction are also a function of these local sample characteristics. The changing index of refraction can be measured using a radiation probe which is reflected off the surface of the sample. Changes in the radiation probe are then monitored to evaluate the sample.

Having described the apparatus for carrying out the subject invention is detail, our present understanding of the mathematics of plasma waves will be set forth. As discussed above, it is well known that the absorption of an intensity modulated energy beam (e.g., electron or laser) results in a modulated temperature profile within the heated material having the properties of a critically damped propagating wave, that is a thermal wave (A. Rosencwaig, *Photoacoustics and Photoacoustic Spectroscopy,* (Wiley, New York, 1980)). Mathematically, the thermal wave is similar to a conventional wave and being dependent upon the thermal properties of the medium for its propagation, it undergoes reflection and refraction at thermal boundaries, and a diffraction from the edges of thermal features. Being critically damped, the thermal wave has the added feature of becoming negligibly small at distances beyond one or two thermal wave lengths from its source. However, by selecting the appropriate modulation frequencies of the source beam and consequently the appropriate thermal wavelengths, the near-surface region within a material can be probed with thermal waves, while maintaining high spatial resolution.

Recently, a number of applications of thermal waves in semiconductor materials have been demonstrated (A. Rosencwaig, Science 218, 223 (1982); W. B. Jackson and N. M. Amer. Phys. Rev. B25, 5559 (1982); A. Rosencwaig, J. Opsal, and D. L. Willenborg, Appl. Phys. Lett. 43, 166 (1983); J. Opsal, A. Rosencwaig, and D. L. Willenborg, Appl. Opt. 22, 3169 (1983); M. A. Olmstead and N. M. Amer. Phys. Rev. Lett. 52, 1148 (1984); W. L. Smith, J. Opsal, A. Rosencwaig, J. B. Stimmell, J. C. Allison and A. S. Bhandia, J. Vac. Sci. Technol. B2, 710 (1984)) and in the process of some of these investigations we have discovered another kind of critically damped wave, in this case a variation in the photo-induced plasma density which can be treated in an analogous fashion to the thermal wave.

By way of introduction, let us consider what happens when a laser beam is incident on a semiconductor. If the energy per photon, E, exceeds the band gap energy, $E_g$, then electrons will be excited from the valence band to an energy, $E-E_g$ above the conduction band edge. These photo-excited carriers, will, within a relatively short time ($10^{-13}$ sec), give up a portion of their energy ($E-E_g$) to the lattice through nonradiative transitions to the unoccupied states near the bottom of the conduction band. After a much longer time ($10^{-3}-10^{-8}$ sec) these photo-excited carriers will recombine with holes in the valence band. Prior to this recombination, there thus exists a plasma of electrons and holes whose spatial density is governed by diffusion in a manner analogous to the flow of heat from a thermal source. Thus, if an incident laser beam is intensity-modulated, we would except to observe, in addition to the thermal wave, a modulated plasma density whose spatial profile is that of a critically damped wave, i.e., a plasma wave.

In order to estimate the significance of this plasma wave, consider first the heat equation in one dimension, $$\delta^2 T/\delta x^2 - (\rho c/\kappa)\delta T/\delta t = -Q_o/\kappa \tag{5}$$

which, assuming a sinusoidal time dependence, $e^{-iwt}$, leads to the equation for thermal waves, $$d^2T/dx^2 + q^2T = -Q_o/\kappa \tag{6}$$

where q is the thermal wave vector defined by $$\begin{aligned} q &= (1 + i)(\omega\rho c/2\kappa)^{\frac{1}{2}} \\ &= (1 + i)/\mu_t \end{aligned} \tag{7}$$

$\kappa$ is the thermal conductivity, and $Q_o$ is the heat source for which we have assumed a sinusoidal time dependence of the form $e^{-iwt}$. In Eq. (7), $\kappa$ is the density, C is the specific heat and $\mu_t$ is the thermal diffusion length. If we now assume that the thermal source is localized at the surface, $x=0$, of a semiinfinite material, then we have the solution, $$T(x) = T_o e^{iqx}, \tag{8}$$

where $T_o$ is the temperature at the surface, $$T_o = iQ_o/q\kappa. \tag{9}$$

For the plasma wave we now have the analogous plasma wave equation, $$d^2N/dx^2 + p^2N = -P_o/D. \tag{10}$$

where p is the plasma wave vector defined by $$p = (1 + i)((\omega\tau + i)/2D\tau)^{\frac{1}{2}}, \tag{11}$$

D is the ambipolar diffusion coefficient, and $P_o$ is the plasma source term. Also, in Eq. (11), $\tau$ is the recombination time. The one essential difference between the plasma wave problem and the thermal wave problem is the existence of the recombination time. In the limit $\omega\tau<<1$, the plasma wave loses its wavelike properties becoming a purely diffusive phenomenon with a plasma diffusion length $l_p=(D\tau)^{\frac{1}{2}}$. However, in Si (S. M. Sze, *Physics of Semiconductor Devices,* Wiley Interscience, New York, 1969, chapt. 2) and for modulation frequencies in the MHz regime, we have $\omega\tau>1$ (in many cases $\omega\tau>>1$), and the plasma density is then governed primarily by lossless diffusion analogous to the thermal wave. In this limit it is meaningful to introduce an additional diffusion length, the plasma wave diffusion length $\mu_p=(2D/\omega)^{\frac{1}{2}}$, which we see is formally identical to the thermal wave diffusion length by replacing the thermal diffusivity, $\kappa/\rho C$, in Eq. (7) by the ambipolar diffusion coefficient, D. As in the thermal wave problem, if we assume that all of the plasma is created at $x=0$, then we have for the plasma density, $$N(x) = N_o e^{ipx} \qquad (12)$$

where $N_o$ is the plasma density at $x=0$, $$N_o = iP_o/pD \qquad (13)$$

If we now let Q denote the total energy flux absorbed in the sample then in terms of Q we have, $Q_o = (-(E-E_g)/E))Q + E_g N/\tau$ and $P_o = Q/E$. If the plasma diffusion length, $l_p = (D\tau)^{\frac{1}{2}}$, is much longer than the thermal diffusion length $\mu_t$, which is often the case for intrinsic Si, then $Q_o = ((E-E_g)/E)Q$. That is since $l_p \gg \mu_t$, the energy in the plasma, $(E_g/E)Q$, which is given up to the lattice as heat when the electrons and holes recombine nonradiatively, is now spread over a distance much greater than the thermal diffusion length and its contribution to the temperature profile (thermal wave) is therefore negligible.

As an example, let's consider a beam of 2.4 eV photons with an absorbed intensity $\simeq 10^5$ W/cm$^2$ in Si as might be obtained from a 5 mW Ar$^+$ laser beam at 514-nm that is focused to a 1 micron radius. Using the literature parameters for intrinsic Si (Sze, supra); $\rho = 2.33$ gm/cm$^3$, C=0.703 J/gm-°C., $\kappa = 1.42$ W/cm-°C., D=20 cm$^2$/sec, $\tau > 10$ $\mu$ sec, and $E_g = 1.1$ eV, we have for the magnitudes of the surface temperature and surface plasma density oscillations at a 1 MHz modulation frequency, $$T_o 14° C.$$

$$N_o = 2.3 \times 10^{19}/\text{cm}^3.$$

These temperature and plasma oscillations, that is, the thermal and plasma waves, are of course, of practical significance only if they can be detected and measured. One effect of an increasing temperature in a semiconductor such as Si is a narrowing of the band gap and consequently, an increase in the optical reflectivity. Measurements over a wide range of energy and temperature yield a coefficient of thermal reflectance in Si (H. A. Weakliem and D. Redfield, J. Appl. Phys. 50, 1491 (1979)) of $(1/R_o)(dR/dT) = 1.5 \times 10^{-4}/°C$. where $R_o$ is the surface reflectance in the absence of any temperature change. Thus, we would expect to observe an amplitude modulation in the optical reflectivity of Si, $DR/R_o \simeq 2.1 \times 10^{-3}$ arising from the surface temperature modulation. In a recent paper on thermal wave effects in metals, (A. Rosencwaig, J. Opsal, W. L. Smith, and D. L. Willenborg, Appl. Phys. Lett., Vol 46 page 1013, 1985) we have shown that such thermal wave induced changes in optical reflectance are readily measured. Here, however, we also must consider the effects of the plasma on the optical reflectivity. This is basically a Drude effect with a negative coefficient of reflectance which has been discussed (A. M. Bonch-Bruevich, V. P. Kovalev, G. S. Romanov, Ya. A. Imas, and M. N. Libenson, Sov. Phys. Tech. Phys. 13, 507 (1968)) and observed using intense laser pulses of picosecond (D. H. Auston and C. V. Shank, Phys. Rev. Lett. 32, 1120 (1974); J. M. Liu, H. Kurz, and N. Bloembergen, Appl. Phys. Lett. 41, 643 (1982)) and femtosecond (C. V. Shank, R. Yen, and C. Hirlimann, Phys. Rev. Lett 50, 454 (1983)) duration. For a He-Ne laser probe beam of wavelength, $1=633$ nm, only the real part of the index of refraction in Si is significant. Thus, for the plasma coefficient of reflectance we have $(1/R_o)(dR/dN) = -2\lambda^2 e^2/\pi n(n^2-1)mc^2$, where n=3.9 is the index of refraction, $e=4.8 \times 10^{-10}$ esu is the electron's charge, $m=0.15$ $m_o$ is the effective mass in terms of the bare electron mass $m_o = 9.1 \times 10^{-28}$ gm, and $c = 3.0 \times 10^{10}$ cm/sec is the speed of light. That is, $(1/R_o)(dR/dN) = -9.6 \times 10^{-23}$ cm$^3$, which implies a plasma wave induced modulation in the optical reflectivity of $DR/R_o \simeq -2.2 \times 10^{-3}$. According to this model then, one would expect a net modulation of the optical reflectivity of Si of $\simeq 10^{-4}$. Our experimental results on Si are in agreement with this observation. That is, the reflectance signal we measure is about an order of magnitude smaller than predicted on the basis of there only being a thermal wave present in the material.

To be more realistic, 3-dimensional effects should be included. As described by Opsal et al, (J. Opsal, A. Rosencwaig, and D. L. Willenborg, Appl. Opt. 22, 3169 (1983)) this may be accomplished by a treatment based on a linear superposition of 1-dimensional solutions.

In summary we have introduced a new kind of critically damped wave which we call a plasma wave, present whenever there is a periodic excitation of the plasma density in semiconductors. We have furthermore demonstrated its significance through measurements of the modulated reflectance on two samples of p-type Si. Analogous to the use of thermal waves as a probe of local variations in thermal features, these plasma waves are of great practical significance in that they can be used to detect changes in material properties which affect their propagation. Such features include: lattice defects, ion implantation damage, cracks, voids and delaminations, to name a few. In some cases, for example in ion implanted regions, we expect plasma waves to be affected much more significantly than thermal waves. In general, we believe plasma waves will provide a complementary capability to the thermal waves as a technique for characterizing semiconductor materials.

While the subject invention has been described with reference to preferred embodiments, it is to be understood that various other changes and modification could be made therein by one skilled in the art without varying from the scope and spirit of the subject invention as defined by the claims appended hereto.

We claim:

1. An apparatus for evaluating a sample comprising:
   means for generating an intensity modulated pump beam of radiation for periodically exciting the surface of the sample with an intensity about $10^5$ Watts/cm$^2$ or greater;
   means for emitting a radiation probe beam of a fixed wavelength selected to allow focusing in the micron range;
   means for focusing the probe beam to a radius in the micron range and for directing the focused probe beam within a portion of the surface of the sample which has been periodically excited in a manner such that said probe beam is reflected;
   means for monitoring the variations in the modulated power of said reflected probe beam resulting from changes in the optical reflectivity of the sample; and means for processing the measured power variations of the reflected probe beam to evaluate the sample.

2. An apparatus as recited in claim 1 wherein said pump beam is focused through said focusing means in a manner to be substantially coincident with the probe beam at the surface of the sample.

3. An apparatus as recited in claim 1 wherein said monitoring means is defined by a photodetector.

4. A method for evaluating a sample comprising the steps of:

generating an intensity modulated pump beam of radiation for periodically exciting the surface of the sample with an intensity about $10^5$ Watts/cm$^2$ or greater;

generating a radiation probe beam of a fixed wavelength selected to allow focusing in the micron range;

focusing the probe beam to a radius in the micron range and directing the focused probe beam within a portion of the surface of the sample which has been periodically excited in a manner such that said probe beam is reflected;

monitoring the variations in the modulated power of said reflected probe beam resulting from changes in the optical reflectivity of the sample; and processing the measured power variations of the reflected probe beam to evaluate the sample.

5. A method as recited in claim 4 further including the step of focusing the pump beam in a manner to be substantially coincident with the probe beam at the surface of the sample.

* * * * *